(12) United States Patent
Jackson

(10) Patent No.: US 8,050,750 B2
(45) Date of Patent: Nov. 1, 2011

(54) EVENT DISCRIMINATION USING UNIPOLAR AND BIPOLAR SIGNAL DIFFERENCES

(75) Inventor: Troy E. Jackson, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 375 days.

(21) Appl. No.: 12/360,380

(22) Filed: Jan. 27, 2009

(65) Prior Publication Data

US 2010/0191132 A1  Jul. 29, 2010

(51) Int. Cl.
*A61B 5/04*  (2006.01)
*A61N 1/00*  (2006.01)

(52) U.S. Cl. .............. 600/509; 600/510; 607/9

(58) Field of Classification Search .......... 600/508–521; 607/9–26
See application file for complete search history.

(56) References Cited

U.S. PATENT DOCUMENTS

| | | | |
|---|---|---|---|
| 4,799,486 A | 1/1989 | Dufault | |
| 5,193,550 A * | 3/1993 | Duffin | 600/510 |
| 5,772,693 A | 6/1998 | Brownlee | |
| 6,434,428 B1 | 8/2002 | Sloman et al. | |
| 6,516,225 B1 * | 2/2003 | Florio | 607/9 |
| 7,139,611 B1 | 11/2006 | Kroll et al. | |
| 7,151,958 B2 * | 12/2006 | Hsu et al. | 600/518 |
| 7,167,747 B2 * | 1/2007 | Gunderson et al. | 607/9 |
| 7,184,834 B1 | 2/2007 | Levine | |
| 7,383,080 B1 * | 6/2008 | Kil et al. | 600/510 |
| 7,383,091 B1 | 6/2008 | Chitre et al. | |
| 7,653,430 B2 * | 1/2010 | Marcovecchio et al. | 600/509 |
| 7,933,643 B1 * | 4/2011 | Gill et al. | 600/510 |
| 7,945,314 B1 * | 5/2011 | Snell et al. | 600/510 |
| 2006/0235476 A1 | 10/2006 | Gunderson et al. | |
| 2007/0244521 A1 | 10/2007 | Bornzin et al. | |

FOREIGN PATENT DOCUMENTS

WO  00/47275  8/2000

OTHER PUBLICATIONS

P0033404.01 (PCT/US2010/020696) PCT Notification of Transmittal of the International Search Report and the Written Opinion of the International Searching Authority, Mailed Apr. 13, 2010, 9 pages.

* cited by examiner

*Primary Examiner* — Niketa Patel
*Assistant Examiner* — Catherine Voorhees
(74) *Attorney, Agent, or Firm* — Michael C. Soldner

(57) ABSTRACT

A medical device and associated method discriminate near-field and far-field events by sensing a bipolar signal and a unipolar signal at a tissue site, detecting an event in response to one of the bipolar and unipolar signals, and comparing an event feature determined from the bipolar signal to an event feature determined from the unipolar signal.

22 Claims, 6 Drawing Sheets

EVENT DISCRIMINATION USING UNIPOLAR AND BIPOLAR SIGNAL DIFFERENCES

TECHNICAL FIELD

The disclosure relates generally to implantable medical devices and, in particular, to a method and apparatus for discriminating near-field and far-field sensed events.

BACKGROUND

The depolarization of the atrium is used as a marker of atrial activation in the determination of atrial rate and rhythm in implantable medical devices (IMDs) such as pacemakers, implantable cardioverter defibrillators (ICDs) and implantable cardiac monitors. Typically, a cardiac electrogram (EGM) signal sensed using an electrode positioned along an atrial chamber that exceeds a programmable sensing threshold is sensed as an atrial depolarization or P-wave. Sensed P-waves are used in determining an atrial rate and detecting and discriminating abnormal heart rhythms.

Errors in determining an actual atrial rate result when atrial oversensing or atrial undersensing occurs. One cause of atrial oversensing is the presence of far-field signals exceeding the atrial sensing threshold. Far-field signals can include R-waves corresponding to the depolarization of the ventricles and other physiologic or non-physiologic noise. Far-field R-waves (FFRWs) can have an amplitude similar to P-wave amplitudes in an atrial sensed signal. The programmable atrial sensing threshold may be increased to avoid FFRW sensing however this may result in atrial P-wave undersensing. The detection of FFRWs as intrinsic atrial events can result in inappropriate atrial rate detection and confuse pattern recognition algorithms used for discriminating arrhythmias, leading to unnecessary pacing mode switching and even unnecessary arrhythmia therapy delivered by the IMD. Discrimination of near-field atrial P-waves from FFRWs during atrial flutter or atrial fibrillation can be even more challenging because the atrial P-wave amplitudes are often lower during atrial arrhythmias than during normal sinus rhythm. Reliable discrimination of near-field and far-field signals is needed in the field of cardiac sensing to enable rejection of far-field signals during monitoring of near-field signals. Discrimination of near-field and far-field signals may be useful in a variety of cardiac rhythm monitoring and therapy delivery applications and may be important in other, non-cardiac electrophysiological sensing applications as well.

DETAILED DESCRIPTION

Figure 1:
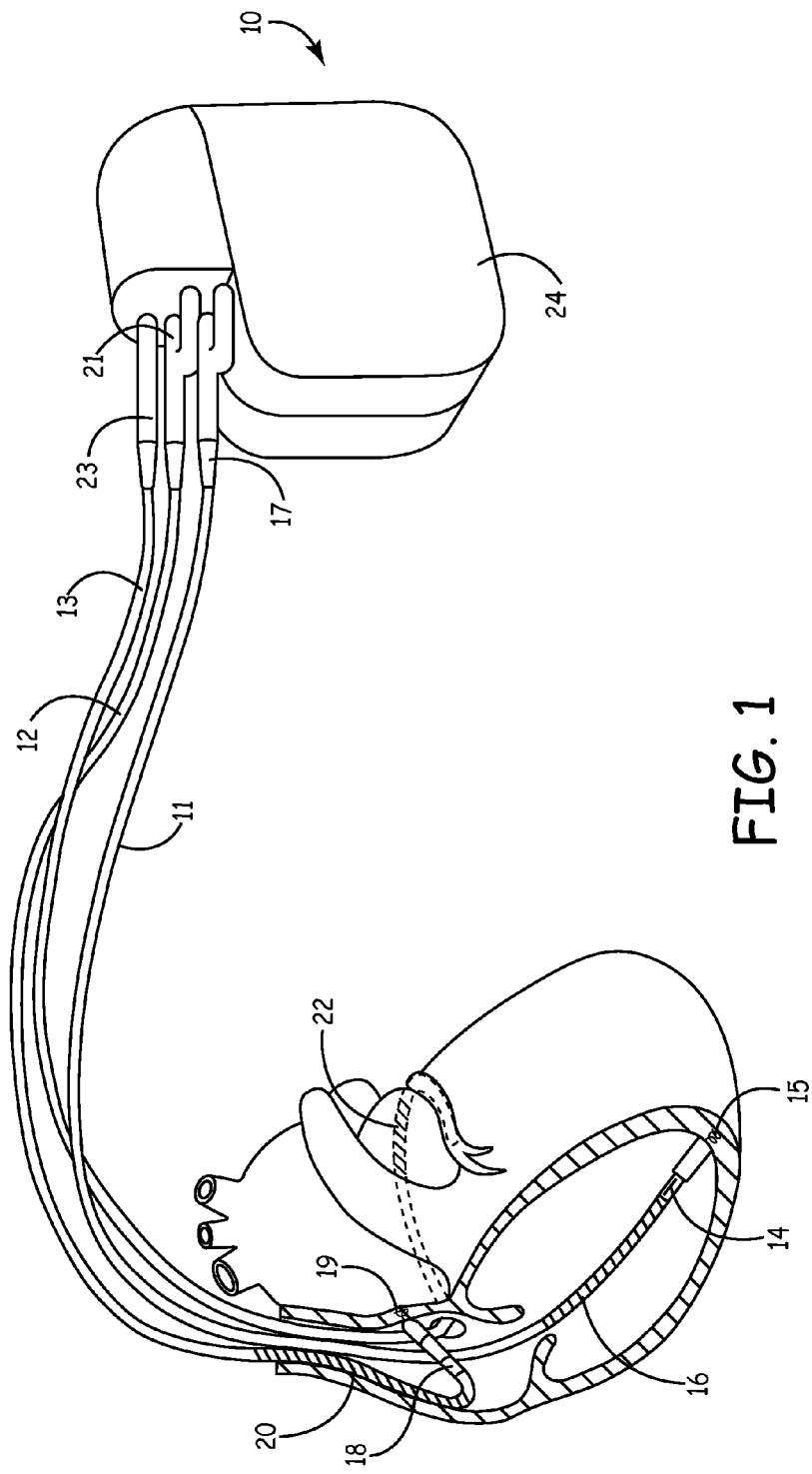
FIG. 1 is a schematic illustration of an IMD system.

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic illustration of an IMD 10, right ventricular lead 11, atrial lead 12, and coronary sinus lead 13. IMD 10 may be capable of delivering electrical pulses for pacing, cardioversion, and defibrillation through leads 11, 12 and 13. IMD 10 determines a need for therapy by sensing cardiac signals using leads 11, 12 and 13. In particular, IMD 10 provides discrimination of near-field and far-field signals based upon a comparative analysis of unipolar and bipolar signals sensed in a cardiac chamber. The comparative analysis generally includes sensing both a bipolar signal and a unipolar signal, determining a feature of a sensed event from both of the unipolar and bipolar signals, comparing the determined features, and confirming that a sensed event is a near-field event based on the comparison. Illustrative embodiments described herein relate primarily to sensing atrial signals and discriminating sensed P-waves from far-field signals. Far-field signals may be FFRWs but may include any physiologic or non-physiologic noise such a myopotential noise or electromagnetic interference. Sensed event discrimination methods described herein, however, may be adapted for use in discriminating near-field and far-field signals in the atria, ventricles or in any other portion of a patient's body, such as in the brain or nervous system or in skeletal or smooth muscles. Methods described herein may be implemented in any medical device that relies on sensing of electrical signals for monitor electrophysiological events.

Right ventricular lead 11 includes a ring electrode 14, tip electrode 15, and elongated coil electrode 16. At the proximal end of right ventricular lead 11 is a bifurcated connection 17, which connects electrodes 14, 15, and 16 to circuitry within device 10. Electrodes 14 and 15 are used to deliver ventricular pacing pulses and for sensing ventricular depolarizations or R-waves in a bipolar sensing configuration. Coil electrode 16 is used to deliver defibrillation or cardioversion shocks. Ventricular tip electrode 15 may also be used in combination with coil electrode 16 for bipolar sensing within the right ventricle or with housing 24 for unipolar sensing of the right ventricular EGM signal for sensing R-waves.

Atrial lead 12 includes a ring electrode 18, tip electrode 19 and coil electrode 20. At the proximal end of atrial lead 12 is bifurcated connection 21, which connects electrodes 18, 19 and 20 to circuitry within IMD 10. Electrodes 18 and 19 are used to deliver atrial pacing pulses and for sensing atrial depolarizations or P-waves in a bipolar configuration. Coil electrode 20 is used for delivering defibrillation or cardioversion shocks. Atrial tip electrode 19 may be used in combination with coil electrode 20 for bipolar sensing in the right atrium or with IMD housing 24 for sensing unipolar atrial signals.

Coronary sinus lead 13 includes coil electrode 22. Coil electrode 22 is advanced within the coronary sinus for positioning in a cardiac vein. At the proximal end of coronary sinus lead 13 is connector 23, which connects electrode 22 to circuitry within IMD 10.

Other lead configurations, electrode configurations, and lead connector arrangements may be substituted for the leads 11, 12 and 13. For example, in a two lead system, atrial defibrillation and sensing electrodes might be added to either coronary sinus lead 13 or right ventricular lead 11 instead of being located on separate atrial lead 12. In any of the configurations, all leads are connected to circuitry within IMD housing 24, which controls sensing and therapy delivery function using selected electrodes, and processes signals sensed by the electrodes.

In some embodiments, IMD 10 may be implemented as a single chamber device for sensing signals (and optionally delivering therapy) in only one or both upper atrial chambers or in only one or both lower ventricular chambers. The sensed event discrimination methods described herein rely on signals sensed in a monitored chamber without sensing signals in the other heart chambers. For example, a single chamber atrial pacemaker may be coupled to an atrial lead including at least a bipolar pair of electrodes for sensing bipolar atrial signals and for sensing unipolar atrial signals using one of the electrodes in combination with the pacemaker housing (or another available reference electrode). Discrimination of P-waves from far-field events is performed using the atrial unipolar and bipolar signals without sensing ventricular signals, i.e., without using a ventricular lead and without necessarily using an electrode positioned in, on, or along a ventricle.

Methods described herein may be implemented in any IMD system including at least one bipolar electrode configuration and at least one unipolar electrode configuration for producing both a bipolar and a unipolar signal for monitoring a heart chamber. Typically a bipolar sensing configuration includes a tip electrode used as the sensing electrode and a ring electrode used as a reference electrode. Typical tip-to-ring spacing is approximately 10 mm but may be greater or less than 10 mm. Other bipolar sensing configurations using any type of available electrodes can be used, however, such as tip-to-coil, e.g., right ventricular tip electrode 15 to coil electrode 16, ring-to-ring electrode when two ring electrodes are available within a given heart chamber, or ring-to-coil, e.g., ring electrode 14 to coil electrode 16. During bipolar sensing, both the sensing electrode and the reference electrode are positioned along a monitored tissue site, such as within a heart chamber or along a nerve branch, such that both electrodes are subjected to change in electrical potential caused by an electrophysiological event in the tissue.

Unipolar sensing electrode configurations include a sensing electrode implanted at a tissue site and paired with a reference electrode implanted away from the tissue site such that the reference electrode is not subjected to changes in electrical potential caused by electrophysiological events occurring at the tissue site. A reference electrode in a unipolar configuration is considered to be positioned far enough away from a signal source that it approximates a zero potential reference (conventionally defined as equivalent to a reference located at an infinite distance). Common unipolar sensing configurations in cardiac sensing applications include a sensing electrode embodied as a tip or ring electrode implanted in or along a cardiac chamber paired with a reference electrode embodied as the IMD housing or a coil electrode implanted in a different cardiac chamber. A sensing electrode may be any available tip, ring, epicardial, or coil electrode implanted in or along a cardiac chamber to be monitored. A reference electrode may be any available electrode implanted in a different cardiac chamber or implanted elsewhere in the body, including subcutaneous electrodes.

Methods described herein discriminate near-field and far-field sensed events using unipolar and bipolar signals sensed at a tissue site. The unipolar and bipolar signals may be acquired using the same sensing electrode paired with a unipolar reference electrode and with a bipolar reference electrode. The unipolar and bipolar signals may alternatively be acquired using two different sensing electrodes implanted in close proximity at a tissue site such that both sensing electrodes are subjected to tissue depolarizations occurring in the tissue in a similar way. One sensing electrode is paired with a reference electrode positioned along the tissue to produce the bipolar signal. The other sensing electrode is paired with a distant reference electrode to produce the unipolar signal. Electrodes used to produce the bipolar and unipolar signals may be positioned along separate leads, a single lead, a bifurcated lead or any lead body configuration enabling deployment of the unipolar and bipolar electrode configurations for sensing at desired a tissue site.

Near-field and far-field event discrimination methods described herein are based on bipolar and unipolar signals differences due to the location of the generating source of the signal. This concept is illustrated using an example of atrial sensing. When sensing bipolar atrial signals, an activation wavefront corresponding to a P-wave will pass by the sensing electrode, e.g. the atrial tip electrode, and the bipolar reference electrode, e.g. the atrial ring electrode, generating a P-wave signal. The P-wave signal is a differential signal produced as the depolarization passes by the sensing electrode and the reference electrode at two different time points. When sensing unipolar atrial signals, the P-wave signal is produced as the wavefront passes the sensing electrode, with the reference electrode approximating a zero reference potential.

In contrast, a far-field event signal will reach both the sensing electrode and a nearby reference electrode of a bipolar sensing pair at approximately the same time with approximately the same amplitude. The same far-field event signal will arrive at the sensing electrode with the same amplitude measured relative to the distant reference electrode approximating a zero reference potential. The differential signal amplitude produced by the bipolar electrode pair will thus be attenuated compared to the signal amplitude produced by the unipolar electrode pair. This difference between bipolar and unipolar far-field signals can be used to discriminate near-field and far-field sensed events. If a sensed event is a near-field event, the amplitude of the event as sensed by the bipolar electrode pair will not be significantly attenuated relative to the amplitude of the event sensed by the unipolar electrode pair. Conversely, if a sensed event is a far-field event, the amplitude of the event on the bipolar signal will be attenuated relative to the amplitude of the event on the unipolar signal.

This relative attenuation of the bipolar signal relative to the unipolar signal can be attributed to the location of the generating source of the signal and thus be used to discriminate near-field and far-field events. The unipolar and bipolar signal differences due to the location of the generating source of the signal can include, but are not limited to, differences in event signal amplitude, event signal width, and event signal slew rate. Accordingly, any of these or other event features may be used for determining differences between bipolar event signals and unipolar event signals for discriminating between near-field and far-field events. As used herein, an "attenuation metric" refers to any metric of the difference between a bipolar event signal and a unipolar event signal sensed at a tissue site. An attenuation metric may be computed as a ratio or a difference between a bipolar event signal feature and the corresponding unipolar event signal feature. An attenuation metric may be computed using one or more events, for example over a series of cardiac cycles.

Figure 2:
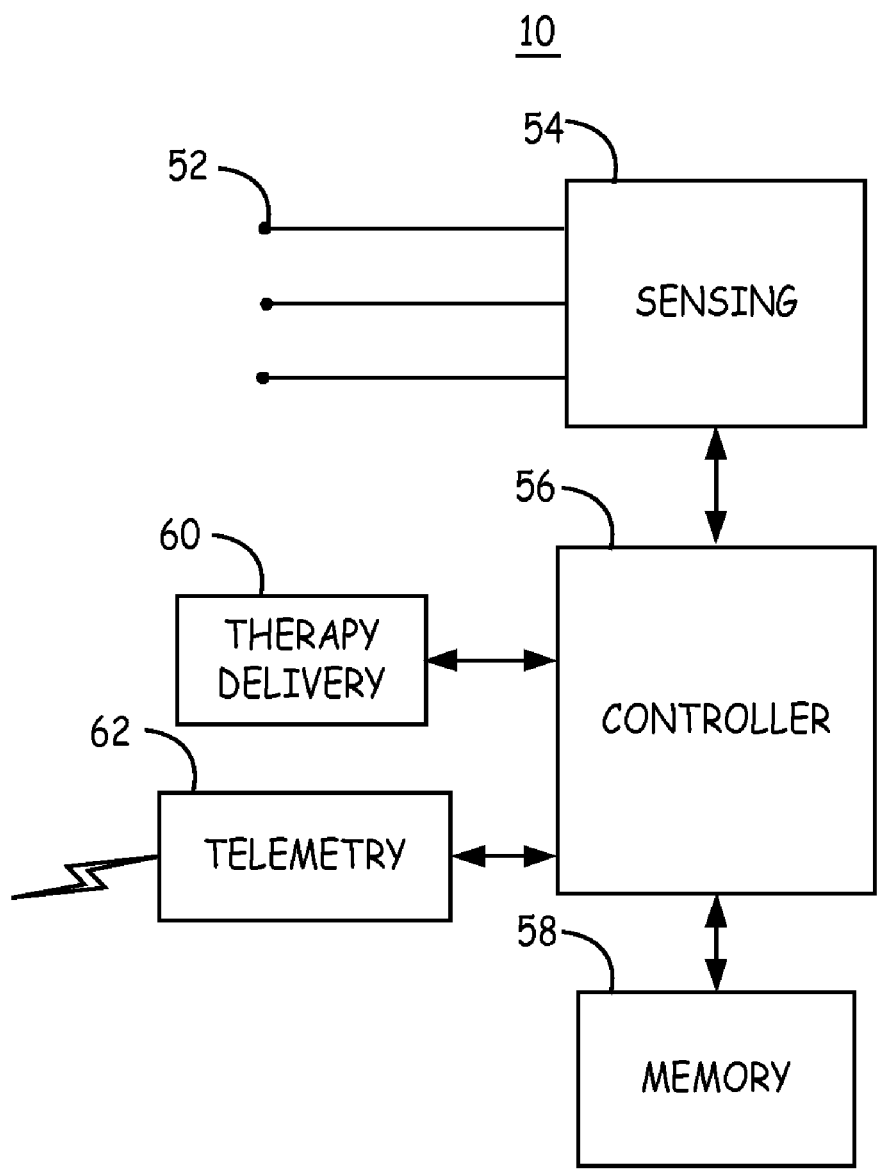
FIG. 2 is a functional block diagram of an IMD.

FIG. 2 is a functional block diagram of IMD 10. IMD 10 includes sensing circuitry 54, controller 56, memory 58, therapy delivery module 60, and telemetry module 62. Sensing circuitry 54 receives signals from electrodes 52, which may include any of the electrodes 14, 15, 16, 18, 19, 20, and 22 shown in FIG. 1. Sensing circuitry 54 generates sensed event signals used by controller 56 for determining a heart rate, classifying heart rhythms, determining a need for therapy, and synchronizing the delivery of therapy with intrinsic cardiac events. Sensed event signals may include sensed atrial event signals corresponding to sensed P-waves in the atrial chambers and sensed ventricular event signals corresponding to R-waves in the ventricular chambers. As will be described herein, sensing circuitry 54 receives at least one bipolar signal and one unipolar signal sensed in a monitored heart chamber for sensing events and discriminating near-field and far-field events. Sensing circuitry 54 may additionally receive signals from other sensors such as a motion, pressure, optical, temperature, pH or other physiological sensors used for monitoring a patient condition.

Sensing circuitry 54 may include any circuitry including analog and digital circuitry required to perform the described functionality. Sensing circuitry may include an application specific integrated circuit (ASIC), an electronic circuit, a processor (shared, dedicated, or group) and memory that execute one or more software or firmware programs, a combinational logic circuit, digital state machines or other suitable components.

Controller 56 analyzes sensed event signals received from sensing circuitry 54 to detect a patient condition using programmed detection algorithms and to make decisions regarding therapy delivery by therapy delivery module 60. Controller 56 may employ a microprocessor and associated memory 58 or digital state machines for performing sensing and therapy delivery functions and controlling other device operations in accordance with a programmed IMD operating mode.

Therapy delivery module 60 may provide electrical stimulation therapy or drug delivery therapy. In one embodiment, therapy delivery module 60 includes a pulse generator for generating low-voltage pacing pulses, e.g., for bradycardia pacing, cardiac resynchronization therapy, and anti-tachycardia pacing, and/or high-voltage pulse generating circuitry for generating high-voltage cardioversion/defibrillation shocks. Though not explicitly shown, it will be understood by one having ordinary skill in the art that therapy delivery unit 60 will be coupled to appropriate therapy delivery elements such as electrodes, catheters, drug delivery ports or the like for administering a therapy.

Telemetry module 62 is provided for bidirectional communication with an external device such as a programmer or home monitor. Physiological signal data, therapy delivery data, and patient-related and device-related diagnostic data may be transmitted to an external device or remote patient management database to allow a clinician access to data acquired by IMD 10. Operating parameters and algorithms may be programmed by transferring data to IMD via telemetry module 62 and stored by memory 58 or implemented by controller 56.

Figure 3:
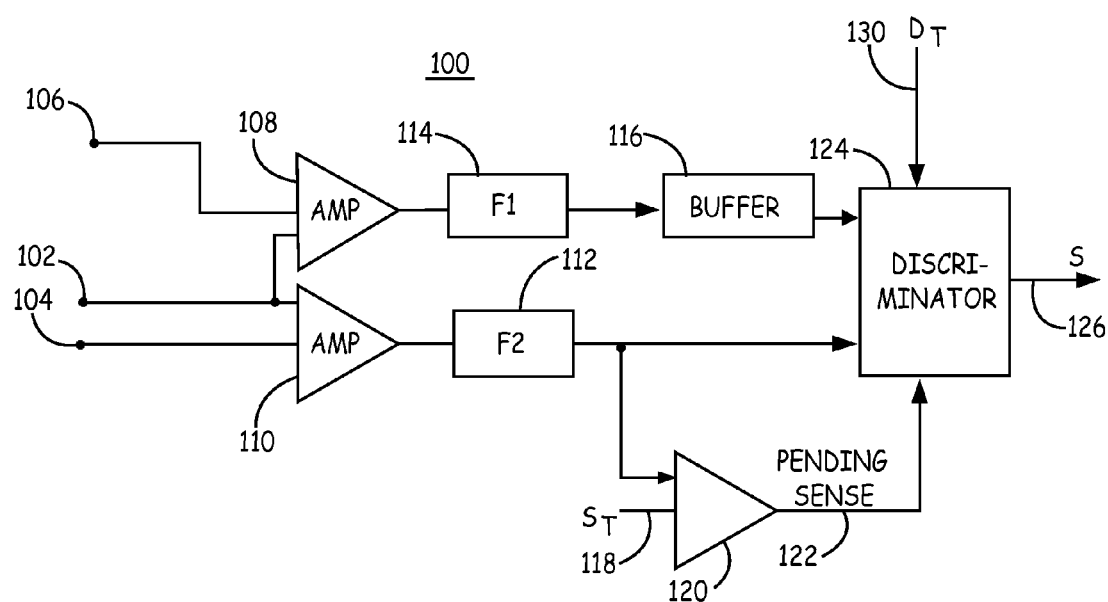
FIG. 3 is a functional block diagram of sensing circuitry included in an IMD for discriminating near-field and far-field events according to one embodiment.

FIG. 3 is a functional block diagram of sensing circuitry included in an IMD for discriminating near-field and far-field events according to one embodiment. Sensing circuitry 100 receives a signal from a sensing electrode 102 paired with a reference electrode 104 forming a bipolar pair of sensing electrodes. In cardiac sensing applications, sensing electrode 102 and reference electrode 104 are positioned in or along the same cardiac chamber in which near-field events are being sensed. In other electrophysiological sensing applications, the sensing electrode 102 and the reference electrode 104 are both positioned along a tissue site generating near-field events such that both electrodes are subjected to passing depolarization wavefronts generated in the tissue.

Sensing circuitry 100 additionally receives signals from sensing electrode 102 paired with a different reference electrode 106 spaced further from sensing electrode 102 than bipolar reference electrode 104. Unipolar reference electrode 106 is positioned away from the tissue generating near-field events, along which sensing electrode 102 is positioned, such at unipolar reference electrode 106 is not subjected to passing depolarization wavefronts generated in the tissue. Reference electrode 106 approximates a zero potential reference located at infinity.

In alternative embodiments, a different sensing electrode may be used in addition to sensing electrode 102 as described previously. The bipolar pair of electrodes and the unipolar pair of electrodes may be unique pairs of electrodes. The sensing electrode for both pairs may be positioned in relative close proximity to each other along the tissue generating the near-field signal being monitored. The two distinct sensing electrodes may be positioned adjacent each other so that both sensing electrodes are subjected to similar changes in electrical potential such that any differences in an event signals sensed on the unipolar and bipolar pairs is primarily due to the location of the generating source of the event signal and the location of the reference electrodes relative to the generating source, not the location of the sensing electrodes themselves.

Sensing circuitry 100 includes a differential sense amplifier 110 receiving signals from the bipolar pair 102 and 104 to produce a bipolar signal. Sensing circuitry 100 includes a second differential sense amplifier 108 receiving signals from the unipolar pair 102 and 106 to produce a unipolar signal. While not explicitly shown in FIG. 3, it is understood that sensing circuitry 100 may include a rectifier(s) to provide a rectified bipolar signal and a rectified unipolar signal.

Sensing circuitry 100 includes bipolar signal filter 112 and unipolar signal filter 114. The bipolar and unipolar signals may be filtered using the same filtering characteristics. For example, a low pass or band pass filter may be used having a low-pass cut-off frequency of approximately 50 to 200 Hz to remove high frequency non-physiological noise from the signals. Alternatively, each of the filters 112 and 114 may be designed to uniquely filter the bipolar and unipolar signals to emphasize the near-field signal component of the bipolar signal and/or emphasize the far-field signal component of the unipolar signal using different filtering characteristics.

For example, knowing the frequency characteristics of far-field R-waves on a unipolar atrial sensing signal, the frequency characteristics of filter 114 may be designed to emphasize the far-field R-wave amplitude without significantly increasing the near-field P-wave amplitude. The bipolar signal filter 112 may be designed to emphasize the near-field P-wave amplitude without significantly increasing the far-field R-wave amplitude. In one embodiment, unipolar signal filter 114 is a bandpass filter having a high pass corner in the range of approximately 5 to 20 Hz and a low pass corner in the range of approximately 40 Hz to 60 Hz. The bipolar signal filter 112 may be a bandpass filter having a high pass corner of approximately 20 Hz and a low pass corner between approximately 60 to 200 Hz. By filtering the unipolar signal in a way that emphasizes the far-field R-wave amplitude without increasing the near-field P-wave amplitude, a ratio of the bipolar to unipolar signal peak amplitudes used as a metric of attenuation of the bipolar signal can promote more reliable discrimination of far-field R-waves and near-field P-waves than using an attenuation metric computed without special filtering.

The bipolar signal is provided to a comparator 120 for sensing events on the bipolar signal which exceed a sensing threshold 118. The sensing threshold 118 may be a programmed or self-adapting threshold. A pending sense signal 122 is provided to a discriminator 124. The unipolar signal is stored in a buffer 116 to provide signal samples to discriminator 124 for a time interval corresponding to the pending sensed event, including signal samples acquired prior to a pending sensed event. As will be further described, discriminator 124 compares the unipolar signal and the bipolar signal over a discrimination time window in response to a pending sense signal 122. It is recognized that a pending event may alternatively be sensed by comparing the unipolar signal to a sensing threshold or using both the bipolar and unipolar signals and corresponding sensing thresholds. As such, the bipolar signal may also be stored in buffer 116 to provide bipolar signal sample values to discriminator 124 during a discrimination time interval corresponding to the pending sensed event.

The discriminator 124 determines when attenuation of the sensed event occurs on the bipolar signal compared to the unipolar signal. As indicated previously, attenuation may be detected based on a difference between the bipolar and unipolar event signal amplitude, event signal width, event signal slew rate or other event signal features. When attenuation of the bipolar event signal is detected, the sensed event is determined to be a far-field signal.

The discriminator may be configured to provide a sense signal 126 in response to not detecting attenuation of the bipolar event signal. The sense event signal 126 may be provided to an IMD controller for detecting a cardiac rate or rhythm or synchronizing electrical stimulation therapies. The discriminator may be configured to reject far-field signals by not producing a sense event signal 126 when attenuation of the bipolar event signal is detected.

Alternatively, the discriminator 124 may be configured to provide unique sense event signals for indicating when a sensed event is a far-field event and when a sensed event is a near-field event. For example, when attenuation of the bipolar event signal is detected when sensing in the atrium, a far-field R-wave sense signal may be generated by discriminator 124. When attenuation of the bipolar event signal is not detected, a P-wave sense signal may be generated. Both far-field events and near-field events may then be used by the IMD controller for determining a heart rate, detecting a heart rhythm, or synchronizing device-delivered therapies with intrinsic cardiac events.

As will be described in greater detail herein, the discriminator 124 detects attenuation of a bipolar event signal using a discrimination threshold 130. Discrimination threshold 130 may be defined as a constant threshold, which may be programmable, or defined as a function of a feature of either the unipolar or bipolar event signals. The discrimination threshold 130 may therefore depend on the value of an event feature. The discrimination threshold 130 may be a function of any event feature, including an event feature used in computing an attenuation metric.

In one embodiment, discriminator 124 computes a ratio of the peak bipolar signal amplitude to the peak unipolar signal amplitude during a discrimination window set in response to the pending sense signal 122. The computed ratio is compared to a discrimination threshold 130 defined as a function of the unipolar peak signal amplitude. The value of the discrimination threshold 130 used for detecting attenuation of the bipolar signal thus depends on the value of the unipolar signal peak amplitude.

Figure 4:
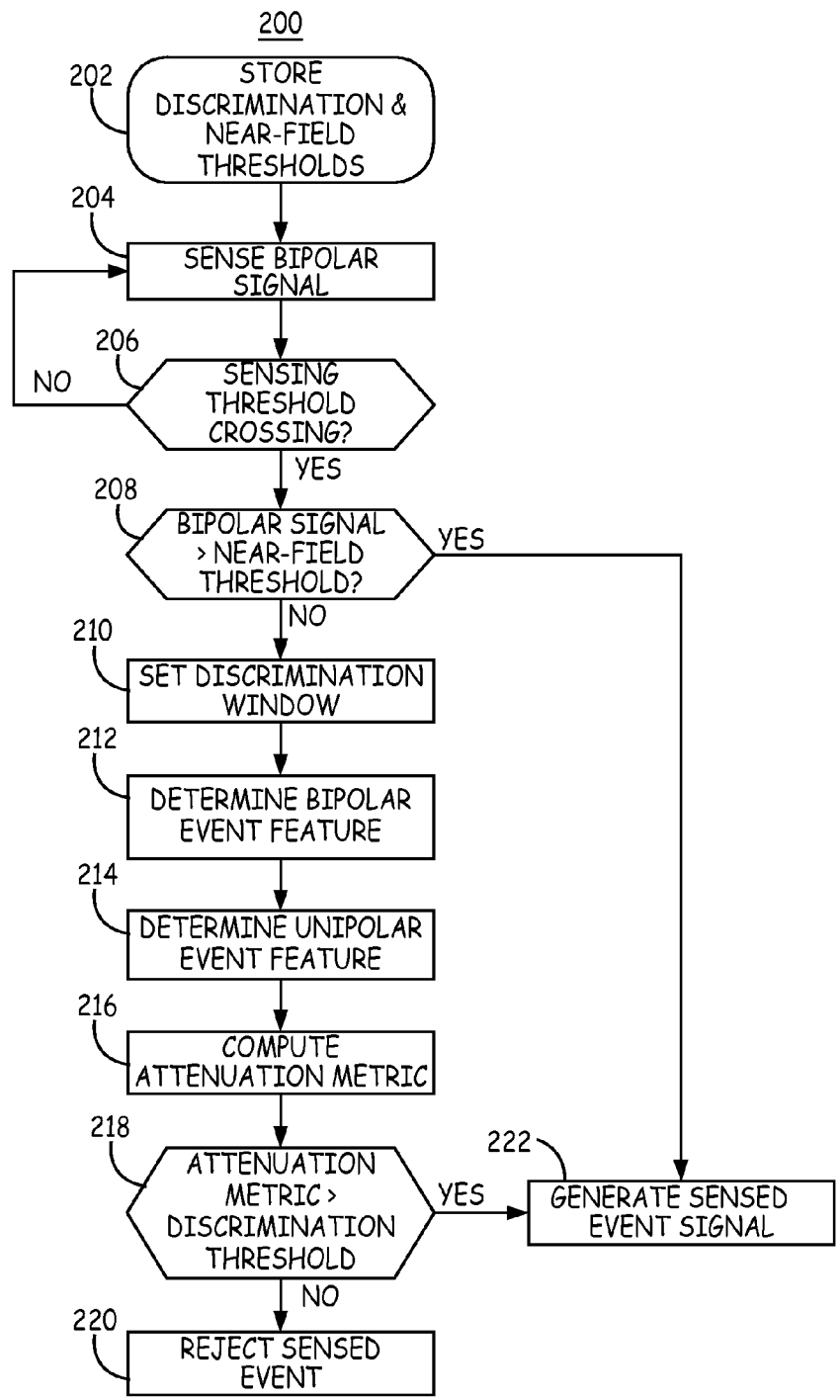
FIG. 4 is a flow chart of a method for discriminating near-field and far-field events performed by sensing circuitry of an IMD.

FIG. 4 is a flow chart of a method 200 for discriminating near-field and far-field events performed by sensing circuitry of an IMD. Flow chart 200 is intended to illustrate the functional operation of the device, and should not be construed as reflective of a specific form of software or hardware necessary to practice the methods described. It is believed that the particular form of software will be determined primarily by the particular system architecture employed in the device and by the particular monitoring and therapy delivery methodologies employed by the device. Providing software, hardware and/or firmware to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 includes a block 202 for storing thresholds used in sensing and discriminating events. In one embodiment, three different thresholds may be defined and stored. A sensing threshold may be programmed for use by sensing circuitry for sensing a pending event. Whenever the bipolar (or unipolar) signal exceeds the sensing threshold, a pending event is sensed. A near-field event threshold may also be programmed and stored for use by sensing circuitry for confirming a sensed event as a near-field event. The near-field threshold defines a signal amplitude which is highly unlikely to be associated with a far-field signal. The near-field threshold is higher than the sensing threshold and any bipolar signal crossing the near-field threshold is confirmed as a near-field event without requiring additional discrimination procedures.

The third threshold stored at block 202 is a discrimination threshold which defines a threshold for an attenuation metric used for detecting attenuation of the bipolar event signal compared to the unipolar event signal. The discrimination threshold may be defined as a fixed programmable value or as a function of an event signal feature, as described above, for example as a function of the unipolar signal peak amplitude.

At block 204, the bipolar signal is sensed. If the sensing threshold is exceeded by the bipolar signal at block 206, indicating a pending sense event, the signal is compared to the near-field threshold. If the bipolar signal exceeds the near-field threshold, as determined at block 208, a sensed event signal is generated at block 222 indicating a near-field event has been sensed. In an illustrative embodiment for discrimination of atrial P-waves from far-field R-waves using atrial unipolar and bipolar signals, the sensing threshold is programmable between 0.15 mV and 0.9 mV and the near-field sensing threshold is programmable between 2 mV and 4 mV. These sample ranges however may vary between embodiments and will depend on electrode type and spacing and device electronics. A bipolar atrial signal exceeding the near-field threshold indicates the pending event is a P-wave signal and is highly unlikely to be a far-field signal. The sensed event signal generated at block 222 is used by the IMD controller in monitoring the patient or in controlling device-delivered therapies.

If the bipolar signal crosses the sensing threshold at block 206 but does not exceed the near-field threshold at block 208, a discrimination window is set at block 210. Since the pending sense event may elicit voltage changes in the bipolar signal at different times than in the unipolar signal, comparisons of the unipolar and bipolar signals for detecting attenuation of the bipolar event signal are not limited to comparisons of simultaneously occurring signal samples. Instead, a discrimination window is set over which event signal features are extracted from both the unipolar and bipolar signals for use in computing an attenuation metric.

In one embodiment, the discrimination window applied to the bipolar signal extends from the sensing threshold crossing to a window end point. The discrimination window applied to the unipolar signal extends from a window start point occurring earlier than the sensing threshold crossing to a window end point occurring after the sensing threshold crossing. The unipolar discrimination window may be centered at the sensing threshold crossing and end at the same time point as the bipolar discrimination window or at a different end point. The duration of the discrimination window(s) applied to the bipolar and unipolar signals will be selected based in part on the filtering applied to the bipolar and unipolar signals and the expected event duration.

At block 212, a bipolar event feature is determined, and at block 214 the corresponding unipolar event feature is determined. The event feature is a feature of the morphology of the event signal and may occur at different times on the unipolar and bipolar signals. In one embodiment, after setting the discrimination window for each signal, extraction of the event features at block 212 and 214 from the bipolar or unipolar signals, respectively, does not require knowledge of the event feature of the other signal or the relative timing between the bipolar and unipolar event signals. In other words, a difference between the time of occurrence of unipolar and bipolar event features, such as a difference between threshold crossing times, peak amplitude times, peak slew rate times or other bipolar and unipolar timing differences do not necessarily need to be determined when determining the event features for computing an attenuation metric.

At block 216, an attenuation metric is computed using the extracted event features. In one embodiment, the event features are determined as the peak bipolar amplitude and the peak unipolar amplitude. The attenuation metric is computed as a ratio of the bipolar peak amplitude to the unipolar peak amplitude. In other embodiments, attenuation metrics may be computed as the ratio of or difference between bipolar and unipolar event slew rates or event signal widths. Attenuation of the peak amplitude, slowing of the slew rate, and widening of the event signal width are each examples of changes in the bipolar far-field event signal relative to the unipolar far-field event signal that are expected to occur. These and other event signal differences between bipolar and unipolar signals may be detected when the far-field event is sensed using a sensing electrode positioned at a sensing site and paired with two different reference electrodes, one spaced from the sensing electrode but in direct contact with the tissue generating near-field signals and one spaced from the sensing electrode and positioned away from the tissue generating near-field signals. Any differences in the morphology of the bipolar event signal relative to the unipolar event signal may be used for computing an attenuation metric at block 216.

At block 218, the attenuation metric is compared to the discrimination threshold. If the attenuation metric crosses the discrimination threshold, the bipolar event signal is attenuated relative to the unipolar event signal indicating the event is a far-field signal. It is recognized that depending on the event feature used and the method for computing the attenuation metric, a near-field signal may be confirmed based on the attenuation metric exceeding the discrimination threshold or falling below the discrimination threshold. The discrimination threshold and the near-field sense event confirmation criteria will be defined according to the attenuation metric used in a given application.

In the example of an attenuation metric computed as the ratio of the bipolar peak amplitude to the unipolar peak amplitude, attenuation of the bipolar event signal is indicated by a decreasing ratio. Thus, if the attenuation metric as ratio of bipolar peak amplitude to unipolar peak amplitude is less than the discrimination threshold (attenuation present), the sensed event is determined to be a far-field event. The pending sensed event may be rejected at block 220 as not being a near-field event. A far-field sense event signal may be generated as described previously. If the attenuation metric is greater than the discrimination threshold (i.e., little or no attenuation), the pending sensed event is confirmed as a near-field event. A sensed event signal is generated at block 222 for use by the IMD controller in monitoring the patient and controlling device-delivered therapies.

Figure 5:
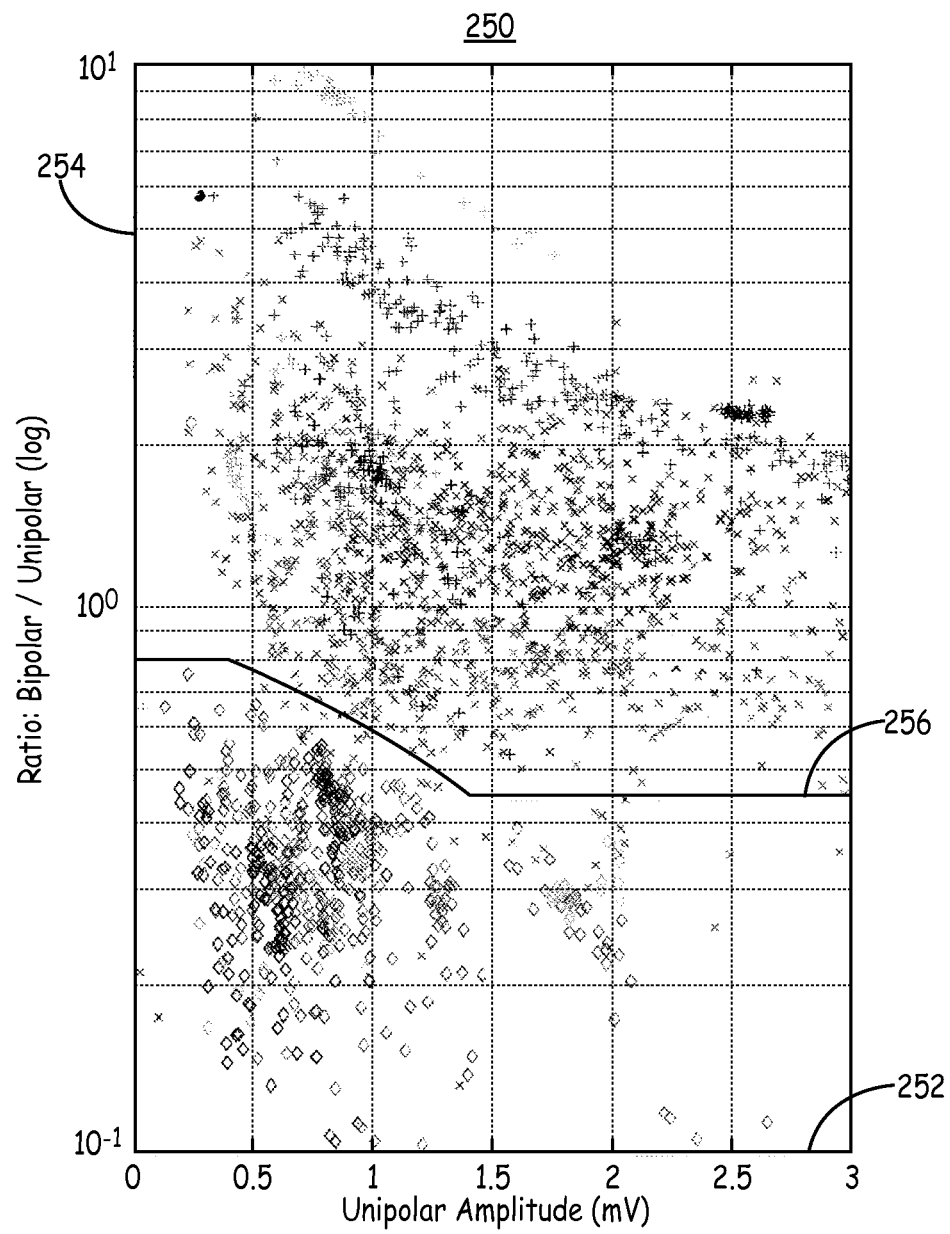
FIG. 5 is a logarithmic plot of attenuation metric values computed using event signal features extracted from bipolar and unipolar signals.

FIG. 5 is a logarithmic plot 250 of attenuation metric values computed using event signal features extracted from bipolar and unipolar signals. To acquire the example data shown, a bipolar atrial signal was sensed using a tip-to-ring sensing configuration with the atrial electrodes positioned along an endocardial lead and spaced at approximately 10 mm. A unipolar signal was sensed using either a tip-to-coil or a tip-to-can (IMD housing) sensing configuration. The unipolar signal was filtered using a 10 Hz to 50 Hz bandpass filter. The bipolar signal was filtered with a passband of 20 Hz to 200 Hz. The attenuation metric was computed as the ratio of the peak bipolar amplitude to the peak unipolar amplitude. The signal peaks were detected during a 40 ms discrimination window following a sensing threshold crossing by the bipolar signal.

In the example plot, the logarithm of the ratio of the peak bipolar amplitude to the peak unipolar amplitude is plotted along the y-axis 254 as a function of the unipolar peak amplitude plotted along the x-axis 252. Events known to be P-waves are plotted using '+' symbols; events known to be far-field R-waves are plotted using diamond-shaped symbols, and events known to be atrial fibrillation are plotted using 'x' symbols. The discrimination threshold 256 is shown by solid line and is defined as a function of the unipolar peak amplitude.

In the example shown, the discrimination threshold (D) 256 is defined as function of the unipolar peak amplitude (u) as follows:

when $u \leq 0.4$ mV, $D(u) = 0.8$;

when 0.4 mV $< u <$ 1.4 mV, $D(u) = -0.35u + 0.94$; and when $u \geq 1.4$ mV, $D(u) = 0.45$.

The discrimination threshold 256 may thus be defined as function of either of the unipolar or bipolar event features or as a constant. As shown, in FIG. 5, the discrimination threshold may be non-linear and may be defined to be a constant over some ranges of an event feature and as a function of the event feature over other ranges of the event feature.

Any events resulting in an attenuation metric below the discrimination threshold 256 will be identified as far-field R-waves. Any events resulting in an attenuation metric above the discrimination metric 256 will be identified as near-field P-waves. As can be observed by the plot 250, the discrimination threshold 256 separates the far-field events and the near field events with a high level of accuracy.

The discrimination threshold 256 may be set as a default function based on data acquired from a patient population or defined manually or semi-automatically for an individual patient using programmable values. For example, bipolar and unipolar signal data acquired by the IMD may be used to generate a plot similar to plot 250 for display to a clinician on an external device. The clinician may manually define a discrimination function based on visual inspection of the plotted data. Confirmation of far-field R-waves may be performed using a ventricular sensed signal or ECG. A discrimination function may alternatively be defined automatically by the IMD during an automatic or semi-automatic learning procedure or using statistical analysis or data modeling techniques.

Figure 6:
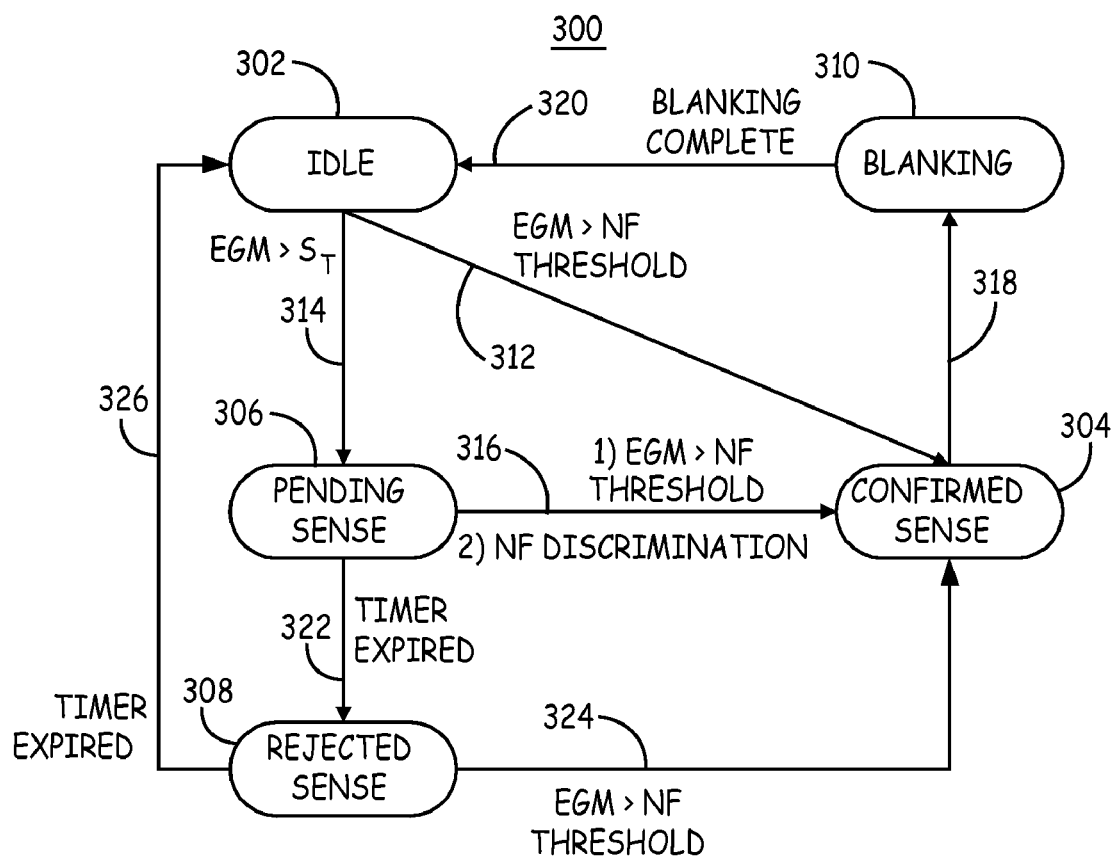
FIG. 6 is a block diagram of a sensing state machine according to one embodiment.

FIG. 6 is a block diagram of a sensing state machine 300 according to one embodiment. The state machine 300 includes an idle state 302, a confirmed sense state 304, a pending sense state 306, and an optional rejected sense state 308, and a blanking state 310. In the idle state, all timers are cleared and the bipolar and unipolar signals are being sensed. A state change 312 from the idle state 302 to the confirmed sense state 304 occurs when the bipolar EGM signal exceeds the near-field sensing threshold. A state change 314 from the idle state 302 to the pending sense state 306 occurs when the bipolar EGM signal exceeds the sensing threshold ($S_T$).

Upon entering the pending sense state 306, a discrimination timer is set. The discrimination timer sets the end point of the discrimination window during which the bipolar and unipolar event features are extracted. During the pending sense state 306, the discriminator performs discrimination operations using the determined event features for discriminating near-field and far-field events as described above.

The pending sense state 306 is exited along state change 316 if the bipolar EGM signal exceeds the near-field threshold at any time during the discrimination window. Upon entering the confirmed sense state 304, a sense signal is generated indicating the pending sense is confirmed as a near-field event. A blanking timer is also set upon entering the confirmed sense state 304. The blanking timer may be set to equal a programmed blanking interval less any time elapsed on the discrimination wait timer.

Upon the next sensed signal sample a state change 318 occurs from confirmed sense state 304 to blanking state 310. During blanking state 310, the blanking timer times out. No events are sensed. Upon expiration of the blanking interval, a state change 320 occurs from the blanking state 310 back to the idle state 302. Upon entering the idle state 302, all timers are cleared and bipolar and unipolar sensing resumes for sensing the next event.

The state change 316 between pending sense state 306 and confirmed sense 304 may also occur when the discrimination timer has expired and the discriminator has confirmed the event as a near-field event according to the discrimination methods described above. Upon expiration of the discrimination timer, without confirmation of the pending sensed event as a near-field event, pending sense state 306 is exited along state change 322 to rejected sense state 308.

Upon entering rejected sense state 308, an additional timer is set as a minimum separation timer to avoid inappropriate sensing of a next event earlier than physiologically possible after the pending sense event. The pending event may remain above the sensing threshold but not meet the criteria required for confirming the event as a near-field event. The rejected sense state timer provides a "safety" blanking interval to avoid sensing the same event twice. The rejected sense state 308 is optional and may be eliminated when the discrimination timer is set during pending sense state 306 to be adequately long enough to ensure that a pending sense event has ended before returning to idle state 302.

In alternative embodiments, instead of setting a discrimination timer to a fixed time interval, a discrimination time interval may determined based on either or both of the unipolar and the bipolar signal amplitudes. A discrimination time interval is set to capture the event signal feature with a high reliability. The discrimination time interval is further intended to prevent a single event from being classified more than once. The discrimination time interval may therefore be set in a variety of ways based on time and/or signal amplitude or other signal features such as dV/dt. For example, when a sensing threshold is crossed, the duration of the pending sensed event may be determined based on a second, negative-going cut-off threshold crossing or a sustained signal amplitude below the cut-off threshold level for a predetermined interval of time. A discrimination time interval may then be set based on the duration of the pending sensed event.

The rejected sense state 308 may be exited if the bipolar EGM threshold exceeds the near-field threshold along state change 324 at any time during the minimum separation timing interval. Otherwise, rejected sense state 308 is exited upon expiration of the minimum separation timer along state change 326.

Thus, a medical device and associated method have been presented in the foregoing description with reference to specific embodiments for discriminating sensed near-field and far-field events. It is appreciated that various modifications to the referenced embodiments may be made without departing from the scope of the invention as set forth in the following claims.

The invention claimed is:

1. A method, comprising:
   sensing a bipolar signal at a tissue site;
   sensing a unipolar signal at the tissue site;
   detecting an event in response to one of the bipolar signal and the unipolar signal;
   determining a first feature of the bipolar signal;
   determining a second feature of the unipolar signal;
   comparing the first feature and the second feature;
   detecting attenuation of the first feature with respect to the second feature; and
   classifying the event as one of a near-field event and a far-field event in response to comparing the first feature and the second feature, the event being classified as a far-field event in response to detecting attenuation of the first feature with respect to the second feature.

2. The method of claim 1 wherein sensing the bipolar signal comprises using a sensing electrode positioned at the tissue site and a first reference electrode spaced a first distance from the sensing electrode, and wherein sensing the unipolar signal comprises using the sensing electrode positioned at the tissue site and a second reference electrode spaced a second distance greater than the first distance from the sensing electrode.

3. The method of claim 1 wherein determining the first feature and the second feature comprises determining a peak amplitude.

4. The method of claim 1 wherein comparing the first feature and the second feature comprises:
   determining a ratio of the first feature and the second feature; and
   comparing the ratio to a discrimination function.

5. The method of claim 4 wherein the discrimination function being defined as a function of one of the first feature and the second feature.

6. The method of claim 1 further comprising:
   setting a first time interval subsequent to detecting the event; and
   determining one of the first feature and the second feature during the first time interval.

7. The method of claim 6 further comprising:
setting a second time interval preceding the detected event; and
determining the other of the first feature and the second feature during a total time interval comprising the first time interval and at least a portion of the second time interval.

8. The method of claim 1 wherein detecting the event comprises:
setting a first sensing threshold for detecting the event;
setting a second sensing threshold greater than the first threshold for confirming the event as a near-field signal;
determining the first and second features in response to the one of the bipolar signal and the unipolar signal exceeding the first threshold and not exceeding the second threshold; and
classifying the event as a near field event when the one of the bipolar signal and the unipolar signal exceeds the second sensing threshold.

9. The method of claim 1 wherein comparing the first and second features comprises:
computing an attenuation metric using the first and second features; and
comparing the attenuation metric to a discrimination threshold.

10. The method of claim 1 further comprising:
setting an event separation time in response to classifying the event; and
not determining the first feature and the second feature during the event separation time.

11. The method of claim 1, further comprising:
filtering the bipolar signal with a first bandpass filter having filter properties that emphasize a near-field event amplitude as compared to a far-field event amplitude; and
filtering the unipolar signal with a second bandpass filter having filter properties different than the first bandpass filter and emphasize a far-field event amplitude.

12. An implantable medical device, comprising;
a plurality of electrodes to sense a bipolar signal and a unipolar signal at a tissue site; and
sensing circuitry configured to detect an event in response to one of the bipolar signal and the unipolar signal, determine a first feature from the bipolar signal, determine a second feature from the unipolar signal, compare the first feature and the second feature, detect attenuation of the first feature with respect to the second feature, and classify the event as one of a near-field event and a far-field event in response to the comparison of the determined features, the event being classified as a far-field event in response to detecting attenuation of the first feature with respect to the second feature.

13. The device of claim 12 wherein the plurality of electrodes comprises:
a sensing electrode adapted to be positioned at the tissue site;
a first reference electrode spaced a first distance from the sensing electrode; and
a second reference electrode spaced a second distance greater than the first distance from the sensing electrode.

14. The device of claim 12 wherein determining the first feature and the second feature comprises determining a peak amplitude.

15. The device of claim 12 wherein comparing the first feature and the second feature comprises determining a ratio of the first feature and the second feature and comparing the ratio to a discrimination function.

16. The device of claim 15 further comprising a memory to store the discrimination function as a function of one of the first feature and the second feature.

17. The device of claim 12 wherein the sensing circuitry sets a first time interval subsequent to detecting the event, and determines one of the first feature and the second feature during the first time interval.

18. The device of claim 17 wherein the sensing circuitry sets a second time interval preceding the detected event; and determines the other of the first feature and the second feature during a total time interval comprising the first time interval and at least a portion of the second time interval.

19. The device of claim 18 wherein detecting an event comprises:
setting a first sensing threshold for detecting the event;
setting a second sensing threshold greater than the first threshold for confirming the event as a near-field signal;
determining the first and second features in response to the one of the bipolar signal and the unipolar signal exceeding the first threshold and not exceeding the second threshold; and
classifying the event as a near field event when the one of the bipolar signal and the unipolar signal exceeds the second sensing threshold.

20. The device of claim 12 wherein comparing the first and second features comprises:
computing an attenuation metric using the first and second features; and
comparing the attenuation metric to a discrimination threshold.

21. The device of claim 20 wherein the sensing circuitry sets an event separation time in response to classifying the event, wherein the sensing circuitry does not determine the first and second features during the event separation time.

22. An implantable medical device, comprising:
means for sensing a bipolar signal at a tissue site;
means for sensing a unipolar signal at the tissue site;
means for detecting an event in response to one of the bipolar signal and the unipolar signal;
means for determining a first feature of the bipolar signal;
means for determining a second feature of the unipolar signal;
means for comparing the first feature and the second feature;
means for detecting attenuation of the first feature with respect to the second feature; and
means for classifying the event as one of a near-field event and a far-field event in response to the comparing the first feature and the second feature, the event being classified as a far-field event in response to detecting attenuation of the first feature with respect to the second feature.

* * * * *